(12) United States Patent
Schoutens et al.

(10) Patent No.: US 11,269,197 B2
(45) Date of Patent: Mar. 8, 2022

(54) GLASSES PROVIDED WITH A LIGHT SOURCE, SYSTEM COMPRISING SUCH GLASSES AND A GLASSES CASE FOR SUCH GLASSES

(71) Applicant: Chrono Eyewear B.V., Tilburg (NL)

(72) Inventors: Antonius Maria Cornelis Schoutens, Tilburg (NL); Hubertus Adrianus Josephus Nicolaas van Berkel, Tilburg (NL)

(*) Notice: Subject to any disclaimer, the term of this patent is extended or adjusted under 35 U.S.C. 154(b) by 645 days.

(21) Appl. No.: 16/090,874

(22) PCT Filed: Apr. 4, 2017

(86) PCT No.: PCT/NL2017/050211
§ 371 (c)(1),
(2) Date: Oct. 3, 2018

(87) PCT Pub. No.: WO2017/176115
PCT Pub. Date: Oct. 12, 2017

(65) Prior Publication Data
US 2019/0179172 A1    Jun. 13, 2019

(30) Foreign Application Priority Data

Apr. 4, 2016 (NL) .................................. 2016539

(51) Int. Cl.
*G02C 11/04* (2006.01)
*G02C 7/10* (2006.01)
(Continued)

(52) U.S. Cl.
CPC ............ *G02C 11/04* (2013.01); *A61N 5/0618* (2013.01); *G02C 7/10* (2013.01);
(Continued)

(58) Field of Classification Search
CPC .......... G02C 11/10; G02C 7/04; G02C 7/101; G02C 11/04; G02C 7/083; G02C 11/00;
(Continued)

(56) References Cited

U.S. PATENT DOCUMENTS

| 4,743,410 A | 5/1988 | Grethen et al. |
| 6,857,739 B1 | 2/2005 | Watson |

(Continued)

FOREIGN PATENT DOCUMENTS

| CN | 201543118 U | 8/2010 |
| CN | 101819334 A | 4/2013 |

(Continued)

*Primary Examiner* — Collin X Beatty
*Assistant Examiner* — Grant A Gagnon
(74) *Attorney, Agent, or Firm* — Khanh T. Glatzel, Esq.; Premium IP Services, P.C.

(57) ABSTRACT

The invention relates to glasses provided with two transparent spectacle glasses enclosed in a frame. Each spectacle glass is positioned in front of a person's eye with the aid of a frame to be positioned on the ears and nose of said person. The glasses are further provided with at least one light source integrated in the frame for directly and/or indirectly delivering light to the eyes substantially from above. A nose frame part of the frame reflects at, at least, a nose frame side portion facing the eye, to the eye at least partially the direct or indirect incident light thereon originating from the light source.

19 Claims, 8 Drawing Sheets

(51) Int. Cl.
*A61N 5/06* (2006.01)
*G02C 11/00* (2006.01)
*H02J 7/02* (2016.01)

(52) U.S. Cl.
CPC ............. *A61N 2005/0626* (2013.01); *A61N 2005/0633* (2013.01); *A61N 2005/0648* (2013.01); *A61N 2005/0651* (2013.01); *A61N 2005/0663* (2013.01); *A61N 2005/0665* (2013.01); *G02C 11/10* (2013.01); *H02J 7/025* (2013.01)

(58) Field of Classification Search
CPC ........ G02C 11/06; G02C 5/143; G02C 7/049; G02C 5/14; G02C 5/001; G02C 7/02; G02C 7/081; G02C 7/085; G02C 2200/02; G02C 5/02; G02C 5/146; G02C 7/022; G02C 7/086; G02C 7/16; G02C 5/22; G02C 7/021; G02C 7/12; G02C 11/08; G02C 2200/08; G02C 2202/16; G02C 2202/22; G02C 3/003; G02C 7/00; G02C 7/046; G02C 7/06; G02C 7/08; G02C 7/088; G02C 7/104; G02C 9/00; G02C 11/12; G02C 13/00; G02C 13/001; G02C 13/003; G02C 13/005; G02C 13/006; G02C 2200/28; G02C 2202/04; G02C 2202/12; G02C 2202/18; G02C 2202/20; G02C 2202/24; G02C 3/00; G02C 3/02; G02C 3/04; G02C 5/008; G02C 5/04; G02C 5/10; G02C 5/12; G02C 5/16; G02C 5/20; G02C 5/2209; G02C 5/2227; G02C 7/061; G02C 7/066; G02C 7/102; G02C 7/105; G02C 7/14; G02C 9/02; G02C 9/04; A61N 1/36046; A61N 1/37276; A61N 1/3787; A61N 2/004; H02J 7/00; H02J 7/0045
USPC ........................................................ 351/158
See application file for complete search history.

(56) References Cited

U.S. PATENT DOCUMENTS

| | | |
|---|---|---|
| 9,532,170 B2 | 5/2016 | Davis |
| 2002/0101568 A1* | 8/2002 | Eberl ................. G02B 27/0172 351/211 |
| 2006/0176442 A1* | 8/2006 | Lee ........................ G02C 11/02 351/51 |
| 2012/0215291 A1 | 8/2012 | Pugh et al. |
| 2014/0072009 A1 | 3/2014 | Wunderer et al. |
| 2016/0016004 A1 | 1/2016 | Hudson |

FOREIGN PATENT DOCUMENTS

| | | |
|---|---|---|
| EP | 2887129 A1 | 6/2015 |
| WO | 8908476 A1 | 9/1989 |
| WO | 2014162271 A2 | 10/2014 |

\* cited by examiner

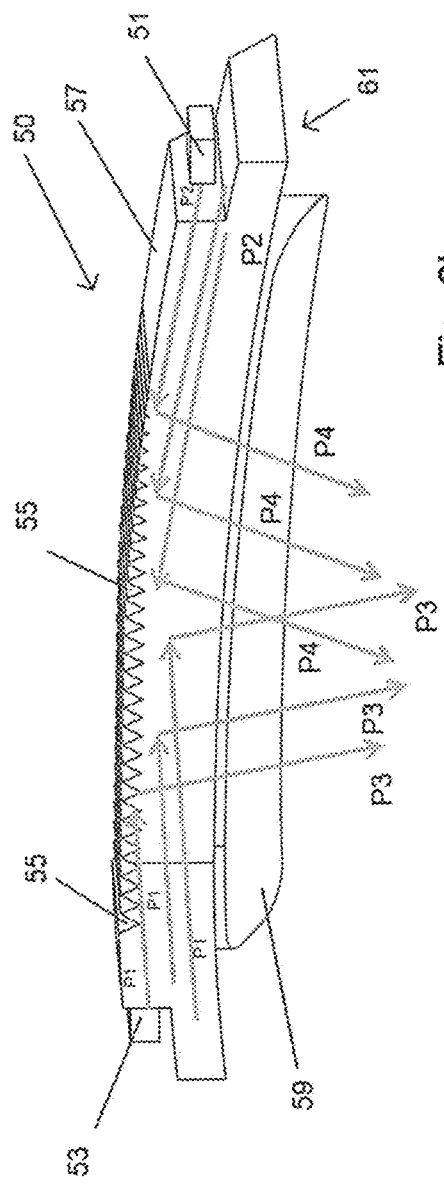
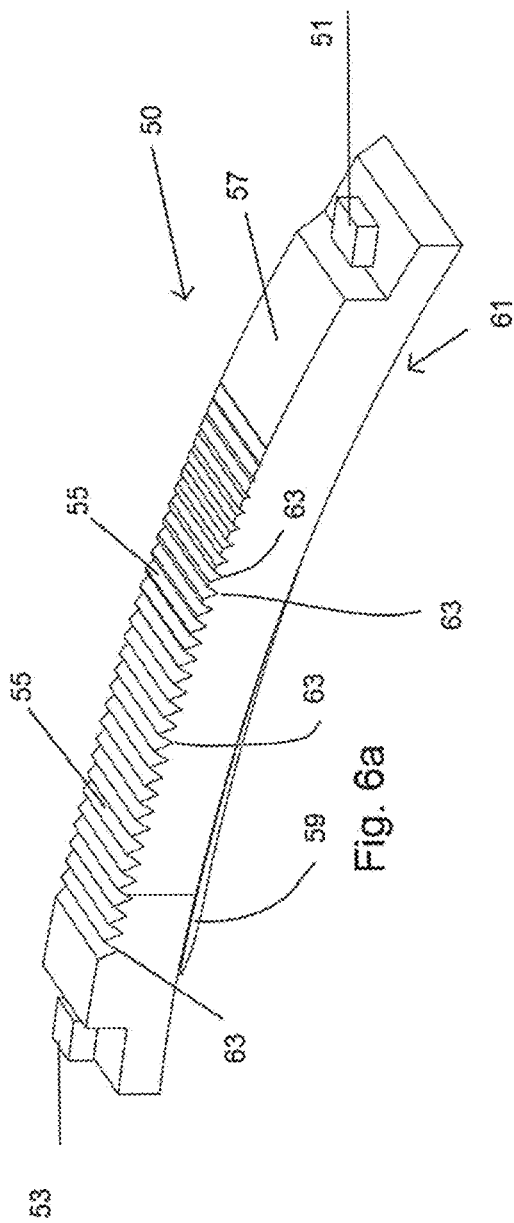

GLASSES PROVIDED WITH A LIGHT SOURCE, SYSTEM COMPRISING SUCH GLASSES AND A GLASSES CASE FOR SUCH GLASSES

CROSS-REFERENCE TO RELATED APPLICATIONS

This application is a national stage filing under 35 U.S.C. § 371 of International Application No. PCT/NL2017/050211, filed Apr. 4, 2017, which was published in English as WO 2017/176115 A1. Each of the above-referenced patent applications is incorporated by reference in its entirety.

The invention relates to a glasses provided with a light source for illuminating at least a portion of the eye of a subject wearing the glasses and relates to a system comprising such a glasses. The invention also relates to a glasses case.

WO2014/162271 shows and describes a light therapy device provided with a frame and a number of light sources. The frame comprises two earpieces, a light emitting panel, a light guiding plate and a nose attachment means for positioning the device onto the nose of the user. FIG. 6 of WO2014/162271 shows an embodiment of the light guiding plate of the light therapy device. This light guiding plate is roughened locally or coated with white paint in order to reflect the light from the light emitting panel to the eyes of the user. During a light treatment the light guiding plate is not transparent, which means that the user of the light therapy device is not able to look through the glass unimpeded due to the reflected light on the coating and/or on the roughness.

It is an aim of the current invention to provide a designer glasses for exposing the eyes to artificial light in a beneficial manner related to energy-consumption and which glasses can be worn continuously without hampering the sight of the wearer during a light treatment.

This aim is achieved with a glasses comprising the aspects as defined in claim 1.

With such a glasses an effective light treatment can be executed, wherein the spectacle glasses are transparent continuously, which means that during the execution of a light treatment with the glasses the wearer can look through the spectacle glasses unhindered and the wearer is capable to perform daily routine tasks. With the artificial light emitted by a light source in the glasses it is possible to influence the circadian rhythm of a wearer of the glasses such that for example discomfort of a jetlag and working in shifts/night shifts can be decreased and/or even be prevented. In order for making the layout of the glasses attractive from the viewpoint of design as less components as possible are assembled in the glasses. Therefore, for example the number of light sources is preferably kept to a minimum, for example at maximum four light sources positioned at a distance from each other which are preferably configured as energy-efficient light-emitting diodes. A minimum number of components in the glasses not only results in a saving of space, though also for a reduction of the energy consumption of the glasses. Herewith the volume and mass of the battery can be kept minimally, which contributes in an enhanced manner to a more compact glasses for the execution of artificial-light treatment. By providing a compact glasses the glasses appears as a regular glasses without light source with regard to design. Herewith the glasses can be worn continuously in the public without standing out that a light treatment can be executed with the glasses. Furthermore the light treatment can be started and terminated automatically at a predetermined time-point without the necessity for the wearer of the glasses to perform an act. In order to guarantee the effective performance of the artificial light in the glasses without being at the expense of the vision through the transparent spectacle glasses or an increased energy consumption, the light originating from the light source is delivered to the eyes directly or indirectly from above, which means that the light is delivered above the spectacle glasses to the eye of the subject wearing the glasses. A wearer of the glasses will experience no hindrance from the artificial light delivered from above to the eyes during a light treatment. The light source will for the purpose be integrated in the portions of the frame positioned above the eyes or in the frame legs, wherein in case of a light source in a frame leg the artificial light is guided to the portions of the frame positioned above the eyes by light guides and subsequently delivered to the eyes in an indirect manner. The delivery of light to the eyes in an indirect manner provides more comfort to the user of the glasses than when the light is guided to the eyes directly via the light source. In order to optimize in the glasses in an energy-beneficial manner the amount of artificial light to the eyes, the lower part of the frame at least comprising the nose frame part is configured such that a nose frame side portion which is at least facing the eye of the wearer reflects at least in part the directly or indirectly incident light originating from the light source. This reflection of the nose frame side portion which is facing the eye of the wearer is at least 50%, preferably more than 85%. This way, artificial light that is lost otherwise during a light treatment is yet reflected to the eyes of the user.

An additional optional feature for the frame of the glasses is that at least portions of the surface of the nose frame side portion which is facing the eye of the wearer reflect the light diffusely. This way the comfort for a user can be increased during a light treatment. Another optional feature is to configure at least portions of the nose frame side portion which is facing the eye of the wearer curved to direct the reflected light specifically to the eye or to a desired location in the eye in order to enhance the effect of the artificial light such that the duration of the light treatment can be shortened, allowing a decrease in the energy consumption of the glasses.

With such a configured glasses a maximum result is achieved in an energy beneficial way with the artificial light emitted by a light source. Lowering the number of components and the total energy consumption of the glasses when in use results in an increased freedom of design for the glasses or sunglasses for executing a treatment with artificial light, such that with regard to the appearance it is possible to establish an attractive designer glasses for the execution of a light treatment.

For example, by using the glasses with artificial light treatment during winter day with relatively short periods of day light, it is possible for the wearer of the glasses' body to artificially lengthen the period of day light during winter, such that the wearer's condition can be improved with the glasses or the energy level of the wearer can be enlarged. In addition, the glasses can be used to optimize the moment at which a performance has to be delivered. For an athlete it is for example not unthinkable that the performance to be delivered takes place for commercial reasons at a time of the day that is less beneficial for the body of the athlete such as for example late in the evening. By using the glasses with the light source therein blue light can be emitted to the eyes of the wearer whereby the production of melatonin is inhibited and the production of cortisol is stimulated at a moment at which presumably the reverse natural effect would occur without glasses. This way, the day-night effects on a human being that regularly hinder a top performance are minimized.

The spectacle glasses can be made of glass or plastic. The spectacle glasses can be connected with each other as one piece.

The use of whitening agents, also referred to as optical brighteners, can enhance the percentage of reflectance of visible light even to above 100 percent. The whitening agents converse invisible ultraviolet light that is harmful to the eye to visible blue light, such that the perceived reflection is higher than the initial amount of light originating from the light source. The whitening agent establishes that radiation is added to the reflection of the visible light.

For simulating a dark environment the glasses can be provided with filter lenses that filter the blue spectrum of the (day) light and the UV light. Transparent red spectacle glasses are for example suitable for simulating a dark environment. This way, the biological production of the hormone melatonin is not suppressed, such that the body receives an endogenous signal to reduce the day time activities and to prepare for the night.

For delivery of light originating from a light source in an indirect way to the eyes a light guiding element can be used. By applying a light guiding element in the glasses the glasses becomes more user friendly during a light treatment because this way direct emission of light originating from the light source is minimized. The light guiding element can be integrated in the frame. The light guiding element comprises notches in an upper surface thereof for reflecting the light originating from the light source when in use to a desired position. When the glasses are worn the light guiding element is located above the eyes. The notches preferably extend transversely to a longitudinal direction of the elongated light guiding element, wherein the notches in the direction of the nose frame part deepen uniformly for reflecting the light originating from the light source to the desired position in the eye. The notches have a triangular cross-section wherein the distance between the centers of the notches is almost constant. This ensures an even distribution of light.

The frame of the glasses can be provided with a support frame for supporting the spectacle glasses. The support frame comprises a support-frame upper portion which is positioned above the eyes when the glasses are worn correctly, and which extends between the frame legs of the glasses. The center of the support-frame upper portion can be connected to the nose frame part. The support-frame upper portion of the glasses can be provided with the above mentioned light guiding element in order to indirectly guide the artificial light from above from the at least one light source to the eyes. Moreover, indirect emission allows for more freedom in design since the position of the light source is optimizable. The light source is for example positioned further away from the eye such that the eye experiences no or just minimal hinder from the warmth produced by the light source.

The support frame of the frame encloses at least half of the perimeter of the spectacle glasses wherein at least the portion of the support frame at eye level when the glasses are worn and/or the portion of the support frame that is located lower than the eye when the glasses are worn reflects the directly or indirectly emitted light from the light source at the side of the support frame that is facing the eye of the wearer. The reflection is at least 50%, preferably more than 85%.

The invention also relates to a system comprising the glasses described in this document with a communication unit and an external device provided with a processor, and in addition a computer program which, when in use, effectuates the processor to control the at least one light source in the glasses according to a predetermined program, wherein preferably the desired program can be selected by the wearer of the glasses. The external device is preferably a portable apparatus such as a smartphone/tablet or the like, wherein the computer program can be an app that is installable on the telephone which app can communicate wirelessly with the glasses via Bluetooth technology, for example to periodically start or to end a light treatment according to a predetermined or selected program.

The invention also relates to a glasses case for a glasses described in this application, wherein the glasses case and the glasses are provided with for example Qi technology such that the battery of the glasses placed in the glasses case is wirelessly chargeable by magnetic induction.

Preferably, the glasses case comprises its own battery such that the portable glasses case can be used for charging the glasses without cables.

Other additional aspects of the glasses are described in the dependent claims.

The glasses is now explained by an embodiment as shown in the incorporated figures, wherein:

FIGS. 6a and 6b show a light guiding element for another embodiment of the glasses;

In the figures, corresponding parts have the same reference number.

Figure 1:
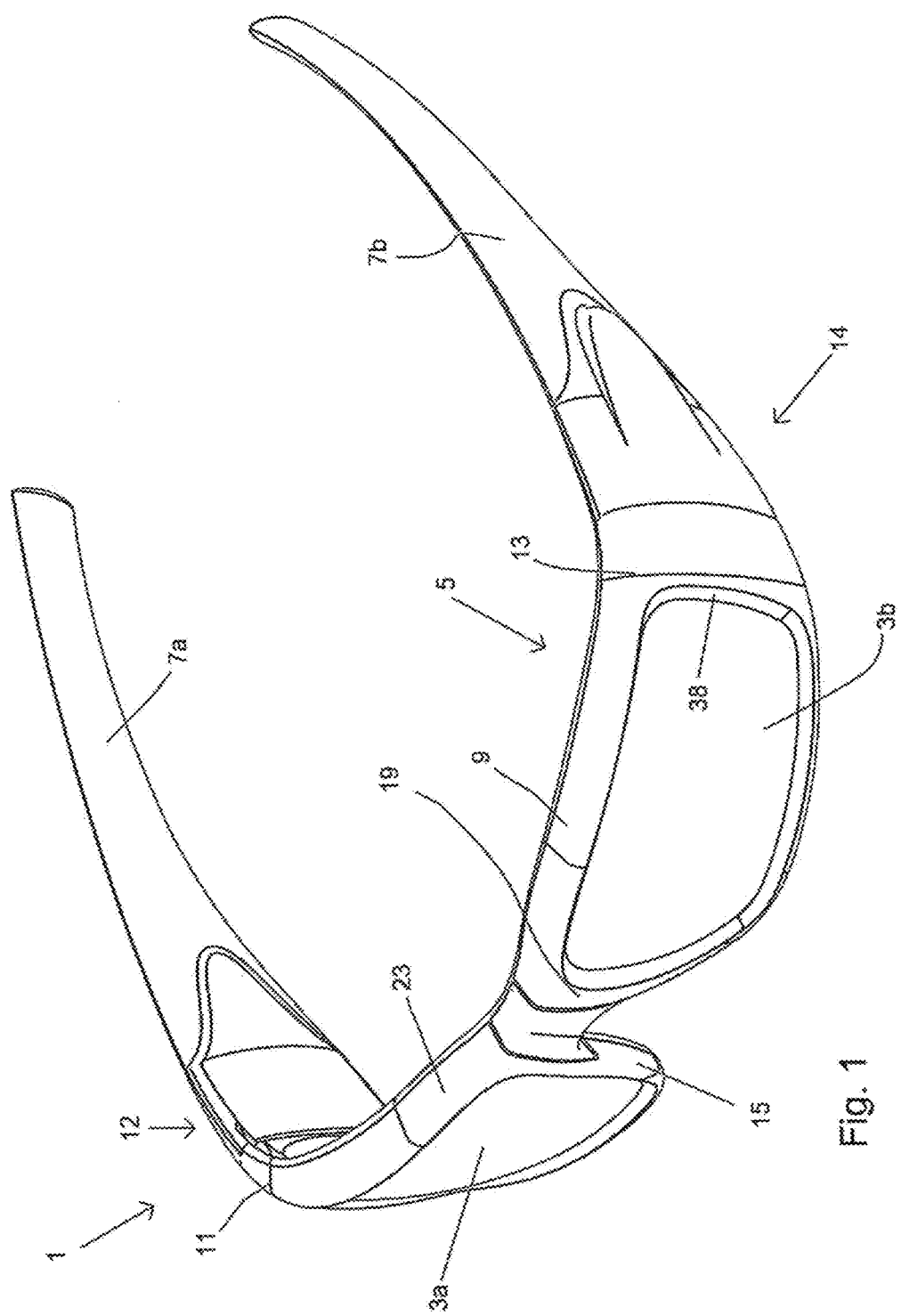
FIG. 1 shows a front perspective view of a glasses.
Figure 2:
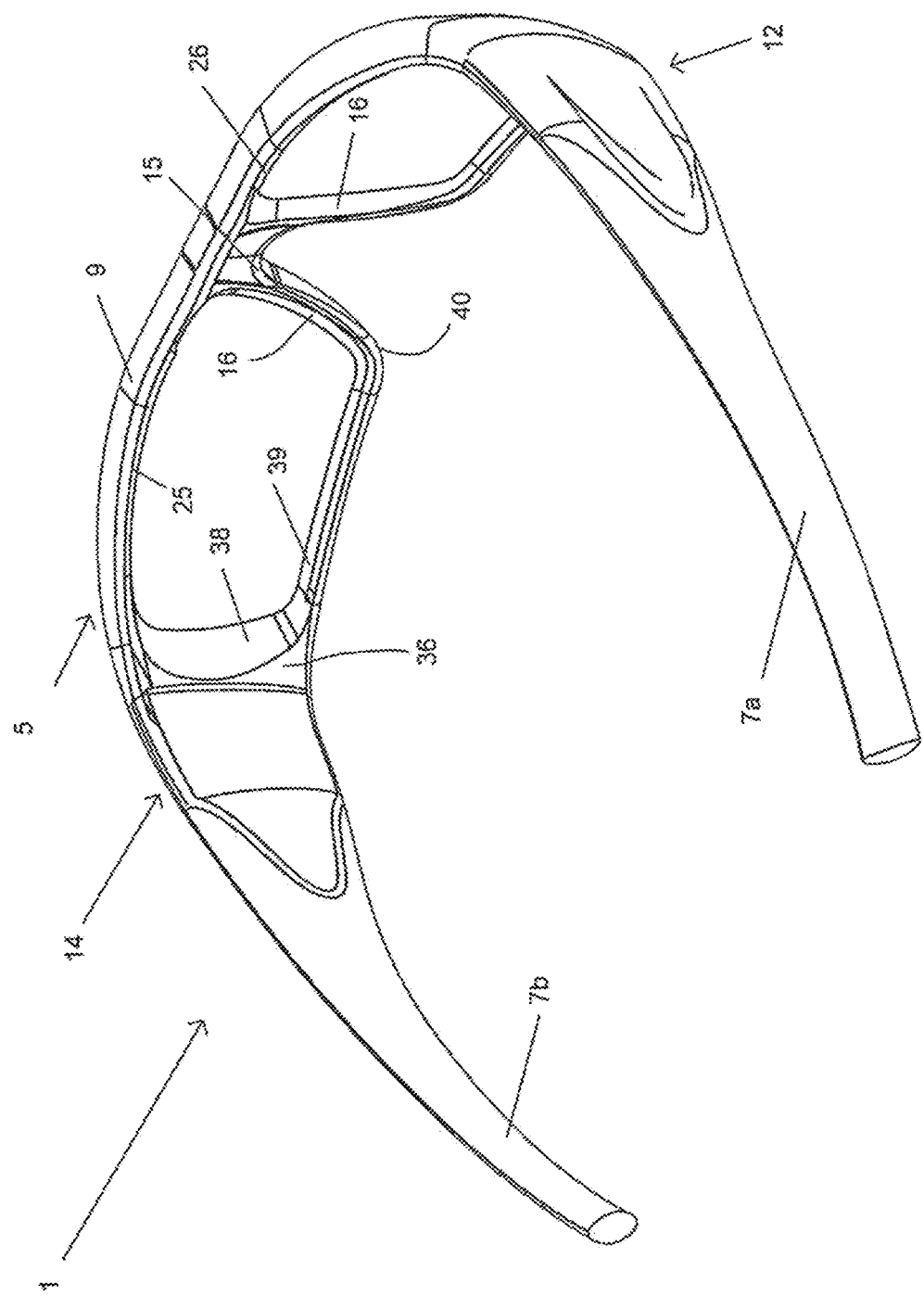
FIG. 2 shows a rear perspective view of a glasses.

The FIGS. 1-5 show a glasses 1 comprising two transparent spectacle glasses 3a, 3b contained by a frame 5. The spectacle glasses 3a, 3b comprise the shape of conventional spectacle glasses. The spectacle glasses 3a, 3b can be made as colored spectacle glasses. Optionally, the spectacle glasses are filter lenses for filtering of blue light and/or UV light, or the spectacle glasses are filter lenses for filtering of red light. The spectacle glasses can be releasably connected to the frame 5, such that the user can exchange the filter lenses for filtering blue light and/or UV light for filter lenses for filtering red light, or, when desired, for conventional spectacle glasses.

The frame 5 further comprises two frame legs 7a, 7b. In the FIGS. 1 and 2 the glasses 1 is shown in use position in which the glasses 1 can be worn by an individual. Each spectacle glass 3a, 3b is positioned in front of one of the two eyes of an individual by frame 5 positioned at the ears and the nose of said individual. The glasses shown in the figures can be provided as sun glasses with spectacle glasses 3a, 3b for sun glasses.

The frame 5 further comprises a support frame 9 for supporting spectacle glasses 3a, 3b. The support frame 9 is connected at a first extremity 11 (left extremity in FIG. 1) with a first frame side part 12 and connected at a second extremity 13 (right extremity in FIG. 1) with a second frame side part 14. The frame side parts 12, 14 are connected to frame legs 7a, 7b at an extremity distal from support frame 9.

The glasses 1 is provided with two light sources (not shown), wherein the first light source in the first frame side part 12 is incorporated into an extremity thereof located near the spectacle glass 3a, whereas the second light source in the second frame side part 14 is incorporated into an extremity thereof located near the spectacle glass 3b.

The light sources are light-emitting diodes (LEDs), which LEDs can emit red and/or blue light. The blue light has a wavelength of 480-700 nanometer. The red light has a wavelength of 660-700 nanometer. It is possible to provide the glasses 1 with blue-light emitting LEDs, only. With the LEDs a light treatment can be performed with the glasses 1, for inhibiting or stimulating the wearer's production of melatonin/cortisol.

The support frame 9 comprises a nose frame part 15. The nose frame part 15 is that portion of the frame 5 which is located around the nose when the glasses 1 is worn by a user. The nose frame part 15 comprises a nose contact surface, a nose frame front side portion 19 directed away from the wearer, an inner surface 16 for supporting a part of the spectacle glass as well as a nose frame side portion 17 facing the eye when the glasses 1 is worn. In the presented glasses 1 the nose contact surface and the nose frame front side portion 19 seamlessly form one piece. The support frame 9 comprises also a support frame upper part 23 which is positioned above the eyes of the wearer when the glasses 1 is worn correctly, and which extents in between frame legs 7a, 7b of the glasses 1. At its center, the support frame upper part 23 is connected with the nose frame part 15.

Figure 3:
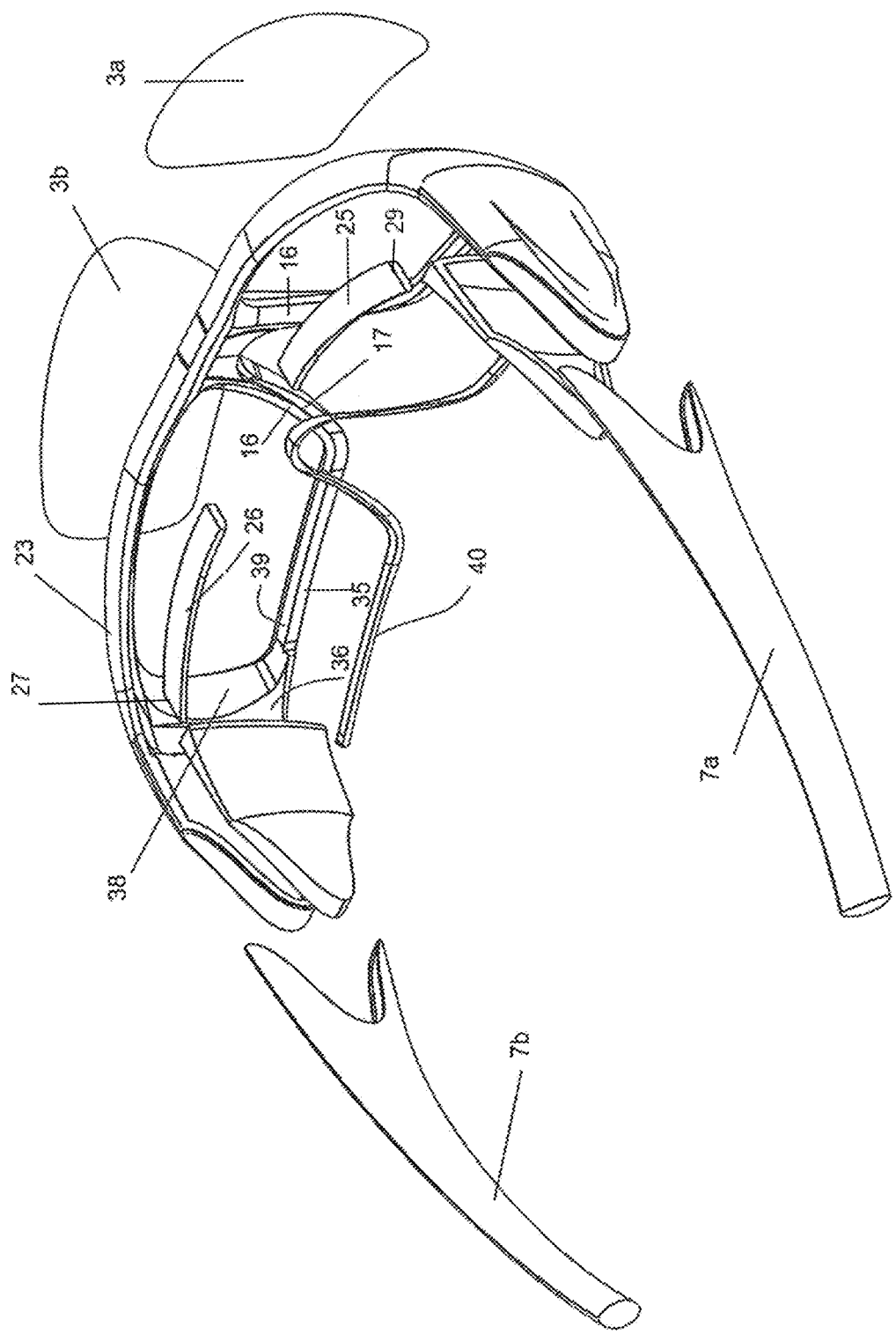
FIG. 3 shows an exploded rear view of the glasses shown in FIGS. 1 and 2.
Figure 4:
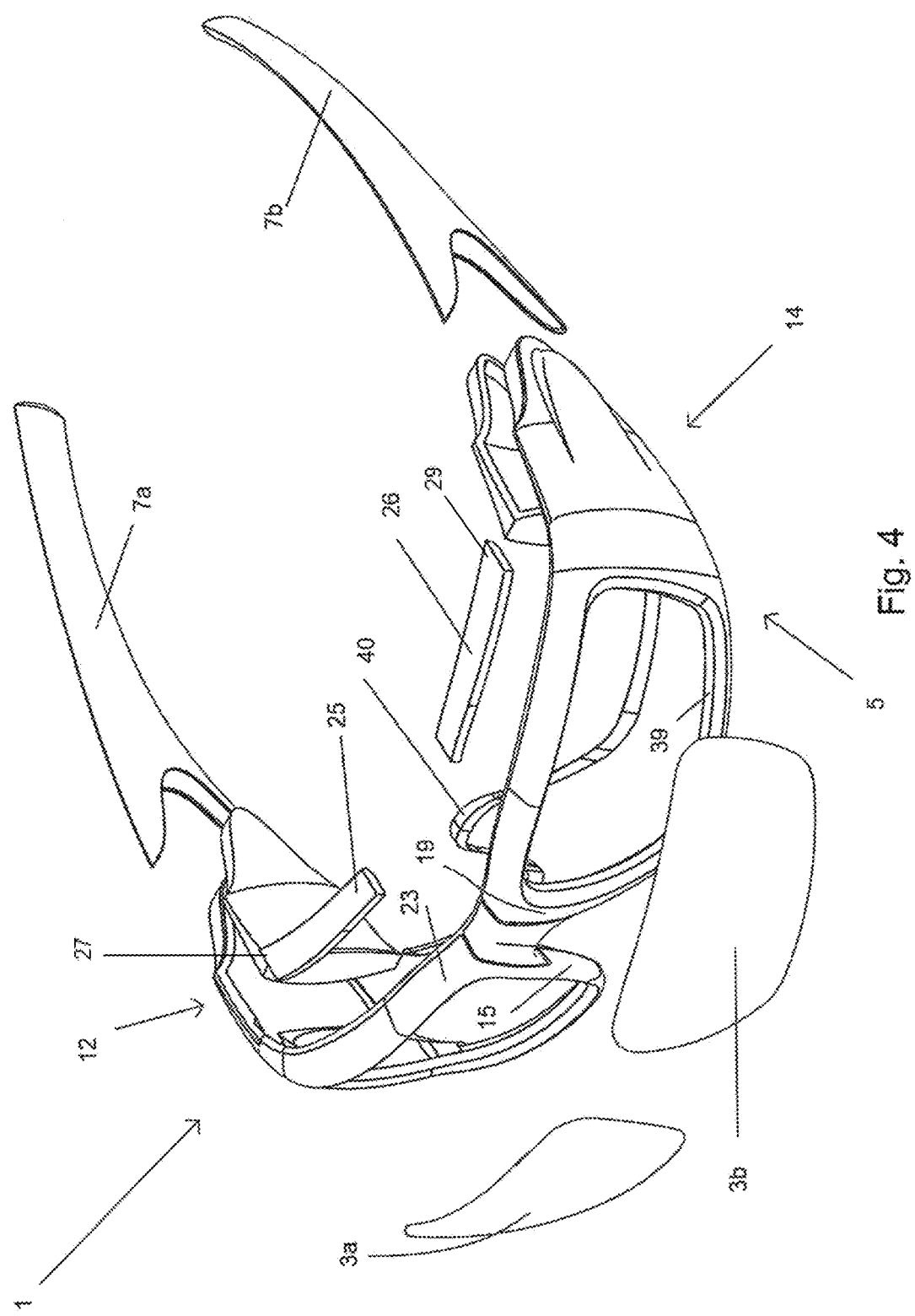
FIG. 4 shows an exploded front view of the glasses shown in FIGS. 1 and 2.
Figure 5:
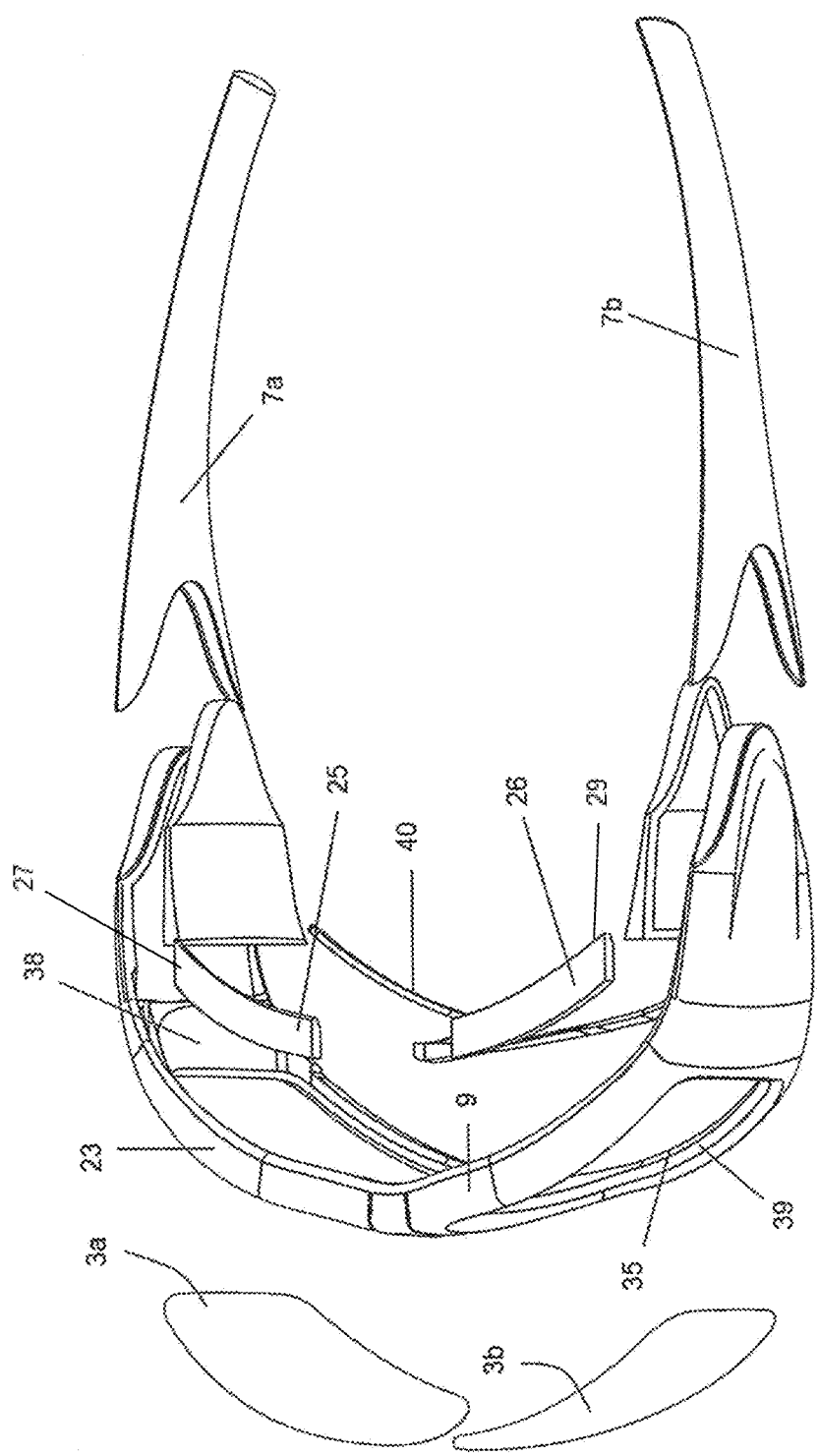
FIG. 5 shows an exploded side view of the glasses shown in FIGS. 1 and 2.

As shown in FIGS. 3-5, the support frame upper part 23 of the glasses 1 is provided with two plate-shaped elongated light guiding elements 25, 26 integrated therein. The light emitted by the LEDs is guided indirectly to the eyes with the light guiding elements 25, 26. An extremity 27, 29 of each light guiding element 25, 26, that is directed away from the nose frame part 15, is in connection with the LEDs in the frame side parts 12, 14 such that the artificial light of the LEDs is emitted indirectly to the eyes from above via the plate-shaped light guiding elements 25, 26 integrated in the support frame upper part 23. It is possible that in the glasses 1 no artificial light is emitted directly from a LED to the eyes of a user, such that the light treatment executed with the glasses 1 is only using indirect light. This way, for the wearer the comfort of the glasses 1 during a light treatment is enhanced.

Figure 7:
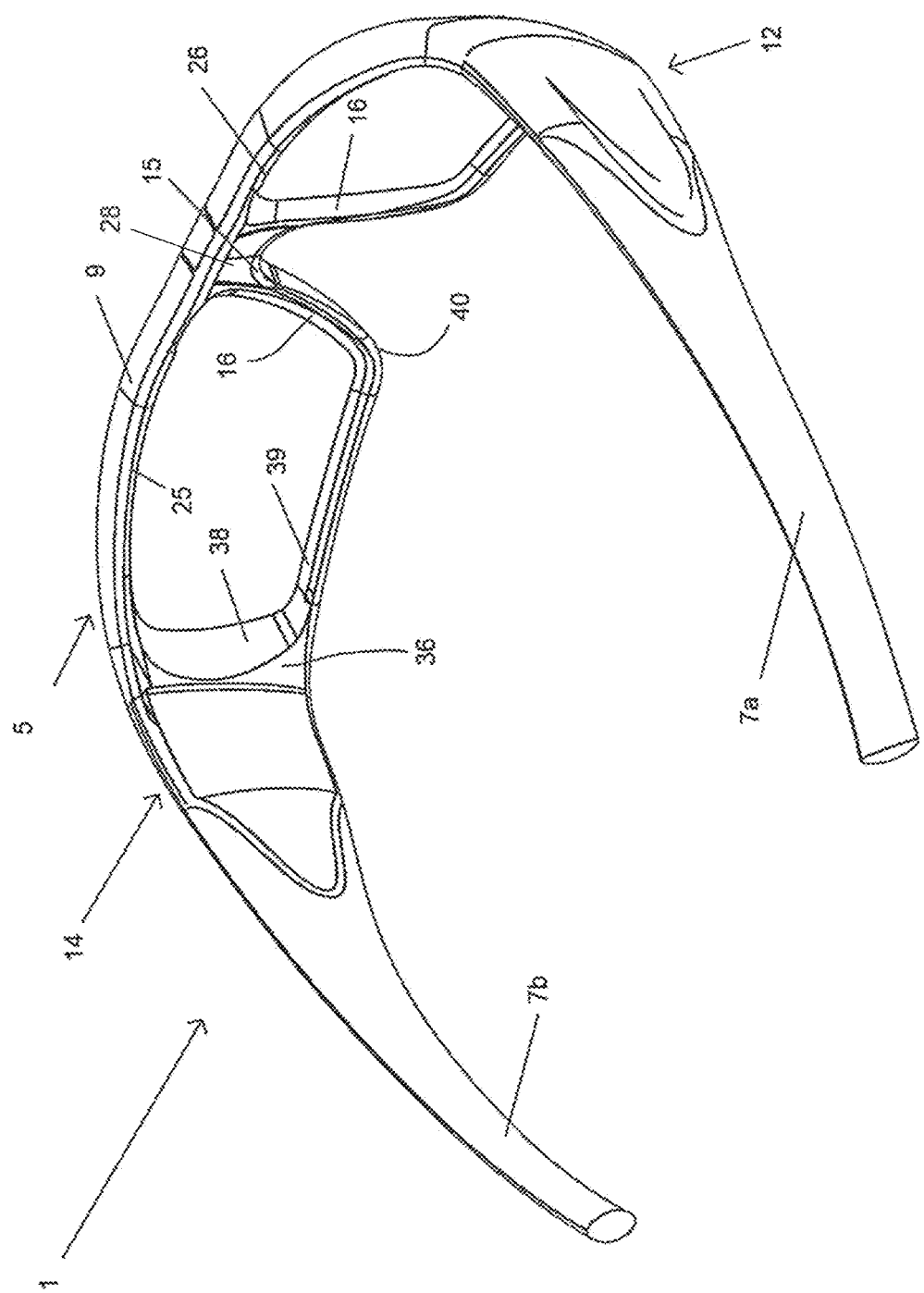
FIG. 7 shows a perspective rear view of a glasses.
Figure 8:
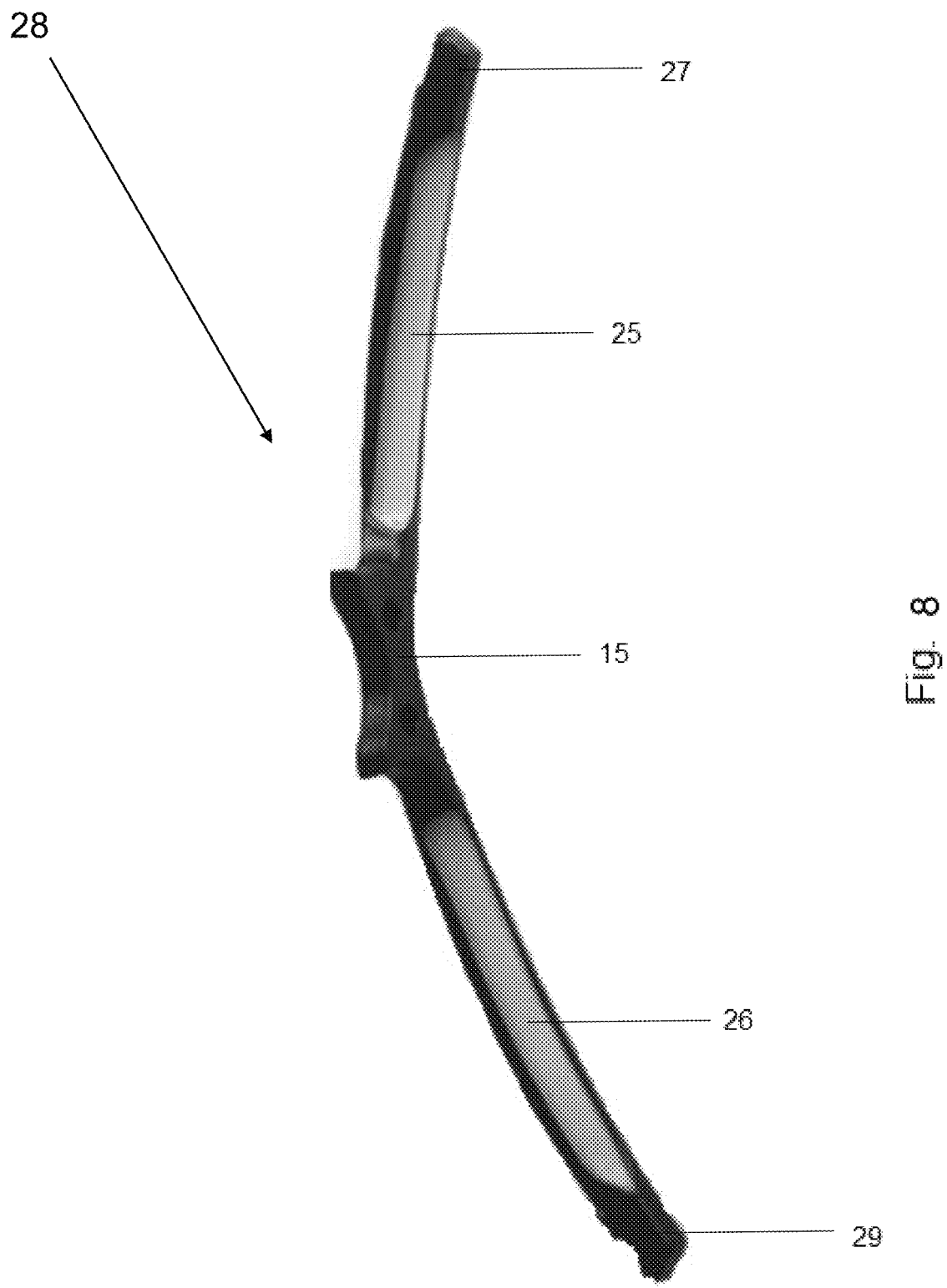
FIG. 8 shows an embodiment of a nose frame part and light guiding elements being a single part.

FIG. 7 shows an embodiment of the glasses of the invention, wherein the nose frame part 15 and the light guiding elements 25 and 26 form a unit 28 with a nose frame part and two light guiding elements. FIG. 8 shows such a unit 28 with a nose frame part and two light guiding elements, according to the invention, wherein the separate parts building up unit 28, namely the nose frame part 15 and the light guiding elements 25 and 26, are indicated. In unit 28 with a nose frame part and two light guiding elements the nose frame part 15 connects the light guiding elements 25 and 26 such that a single part is formed. The application of the unit 28 with a nose frame part and two light guiding elements in a glasses of the invention alternative to a nose frame part 15 and light guiding elements 25 and 26, is optional according to the invention.

The sides of the support frame 9 that are facing the eyes of the wearer and that are positioned below the light guiding elements 25, 26, such as for example the nose frame side portion 17, reflect the artificial light that is coming indirectly from the light guiding elements 25, 26, to the eye of the user. The other sides of the support frame 9 located below the light guiding elements 25, 26, that are facing the eye when in use, can be provided in the same manner as the nose frame side portion 17, such that the amount of light emitted to the eyes is increased. These sides of support frame 9 comprise support frame sides 35, 36 facing the eyes, which extents in the glasses 1 between the nose frame side portion 17 and the support frame upper part 23. The reflecting sides of the support frame 9 can comprise inner surfaces that surround the spectacle glass 3a, 3b, such as the inner surface 16 of the nose frame part and the other inner surfaces 38, 39 of the support frame 9 located below the light guiding elements 25, 26.

In addition, the glasses 1 is provided with a soft lining 40 for enhancing the comfort of the wearer of the glasses 1. Then, it is possible to provide at least the sides of the lining that are facing the eyes as reflecting lining in order to reflect the incident indirect light from the light guiding elements 25, 26 on said sides of the lining, when in use, to the eyes.

The light reflecting parts of the glasses 1, such as the sides of the support frame 9 and/or the lining, reflect the incident light for at least 50%, preferably for more than 85%.

With the glasses of the invention it is possible to project 4 lux at minimum and 6 lux at maximum at the level of the retina, and 36 lux at minimum and 50 lux at maximum at the level of the eye. Said light intensity is essential for executing an effective artificial light treatment.

The FIGS. 6A, 6B show another embodiment of the light guiding element 50. This light guiding element 50 can be assembled in the support frame upper part 23 of the glasses 1 shown in FIGS. 1-5 at the same position as the light guiding element 25, 26.

The elongated light guiding element 50 is provided with a first LED 51, as well as with a second LED 53. For executing a light treatment, with the light guiding element 50 no further light sources are required in the glasses (not shown). The elongated light guiding element 50 is provided with an upper side 57 partly provided with notches 55, as well as a portion 59 protruding at the bottom side 61.

The portions of upper side 57 located nearby the LEDs 51, 53 are flat without notches 55. The notches 55 are provided between the flat portions of the upper side. The portion with notches 55 is larger than the two flat end-portions together. The notches 55 extend transversely to the longitudinal direction of the elongated light guiding element 50. The cross-section of each notch 55 is triangular. The notches 55 become evenly deeper toward the second LED 53, while the distance between the centers 63 of the consecutive notches remains constant.

The LEDs 51, 53 emit the artificial light substantially laterally in the light guiding element 50 in the direction indicated by the arrows P1 and P2 to the notches 55. The artificial light is reflected by the notches 55 in the direction indicated by arrows P3 and P4 to the eye of a user. The light guiding element 50 is preferably made of polycarbonate (e.g., ALCOM pwl 10/1.1 WT1302-05LB). It is possible to add colored or light reflective pigments to the material so that the light can be reflected to the eyes diffusely.

The frame 5 is provided with a control unit such as a circuit board (PCB) and a battery. Optionally, the frame 5 may be provided with a memory storage. These components may be located in the frame side portions 12, 14 or in the frame legs 7a, 7b. Further, the frame may include a communication device (not shown) such as, for example, a USB port for providing a wired connection and/or, for example, a Bluetooth chip for providing a wireless connection.

The glasses 1 may be part of a system further comprising an external device comprising a processor as well as a computer program which, in use, causes the processor to control the LEDs in the glasses in accordance with a predetermined program.

It is possible that the glasses is designed so that the support frame of the frame only partially encloses the perimeter of the spectacle glasses.

It is also possible that at least portions of the surface of the support frame side facing the wearer's eye are designed such that the light to be reflected is diffused. Also, portions of the support frame facing the wearer's eye can be curved such that the light to be reflected is directed to a position in the eye. Further, the side of the support frame facing the wearer's eye may be provided with whitening agents.

The LEDs for emitting the blue light and UV light may be provided with filters for filtering the eye-damaging part of the light spectrum of the light emitted by the light source, such as, for example, UV radiation having a wavelength between 10 and 400 nanometer. These filters can also be provided elsewhere in the glasses to prevent a malicious part of the light emitted with the light source from reaching the eye.

It is further possible to provide the glasses with at least a light source integrated centrally in the frame, for direct and/or indirect delivering light to the eyes substantially from above.

The frame 5 can be provided with two hinging frame legs. In the position of use of the glasses 1 with unfolded hinging frame legs, the glasses 1 can be worn by a person, such that each spectacle glass 3a, 3b is positioned in front of one of the two eyes of a person aided by frame 5 for positioning on the ears and nose of the person. By hinging the frame legs towards each other in the direction of the spectacle glasses 3a, 3b, the glasses 1 is brought from the unfolded state to a compact folded state, such that it is stored, for example, in a glasses case (not shown).

The glasses case and the glasses can be provided with Qi technology such that the battery of the glasses is wirelessly chargeable. Furthermore, the glasses case itself can be provided with a battery such that the glasses case without cables can wirelessly charge the battery of the glasses by using the battery of the glasses case.

An alternative glasses can be provided with two transparent spectacle glasses enclosed in a frame, wherein each spectacle glass is positioned in front of an eye of a person by a frame for positioning on the ears and the nose of said person, the glasses further provided with at least one light source integrated in the frame, wherein above the spectacle glass the frame is provided with at least a light guiding element for indirect delivery of light substantially from above the spectacle glass to the eyes, the light originating from at least one light source. The alternative glasses comprises a light guiding element with notches as herein described and as shown in the Figures. Optionally, the alternative glasses may comprise a frame with a nose frame part, which nose frame part at, at least, a nose frame side portion facing the eye, reflects to the eye at least partially the direct or indirect incident light thereon originating from the light source.

The invention claimed is:

1. Glasses provided with two transparent spectacle glasses enclosed in a frame, wherein each spectacle glass is positioned in front of an eye of a person by a frame for positioning on the ears and the nose of said person, the glasses further provided with at least one light source integrated in the frame for direct and/or indirect delivery of light substantially from above the spectacle glass to the eyes, wherein a nose frame part of the frame at, at least, a nose frame side portion facing the eye, reflects to the eye at least partially the direct or indirect incident light thereon originating from the light source, wherein the frame above the spectacle glass is provided with at least one light guiding element for indirect delivery of light originating from the at least one light source substantially from above the spectacle glass to the eyes, wherein the light guiding element is provided with an upper side having notches, wherein preferably each notch extends transversely to the longitudinal direction of the light guiding element.

2. The glasses of claim 1, wherein the nose frame side portion facing the eye reflects to the eye at least partially the direct or indirect incident light thereon originating from the light source, for at least 50%, preferably for more than 85%.

3. The glasses of claim 1, wherein the frame above the spectacle glass is provided with at least one light guiding element for indirect delivery of light originating from the at least one light source substantially from above the spectacle glass to the eyes.

4. The glasses of claim 1, wherein the notches in the direction of the nose frame part become deeper.

5. The glasses of claim 1, wherein the notches in the direction of the nose frame part become deeper, and wherein the notches in the direction of the nose frame part become evenly deeper.

6. The glasses of claim 1, wherein the notches in the direction of the nose frame part become deeper, wherein the notches in the direction of the nose frame part become evenly deeper, and wherein the distances between centers of the notches are constant.

7. The glasses of claim 1, wherein the light source is at least one light-emitting diode, which light-emitting diode can emit red and/or blue light.

8. The glasses of claim 1, wherein the light source is at least one light-emitting diode, which light-emitting diode can emit red light and/or blue, and wherein the red light has a wavelength of 660-700 nanometer.

9. The glasses of claim 1, wherein the light source is at least one light-emitting diode, which light-emitting diode can emit red light and/or blue, wherein the blue light has a wavelength of 464-480 nanometer, and/or wherein the red light has a wavelength of 660-700 nanometer.

10. The glasses of claim 1, wherein 36-50 lux is deliverable at retinal level with the aid of the at least one light source.

11. The glasses of claim 1, wherein the frame of the glasses is provided with a support frame for supporting the spectacle glasses, wherein the nose frame part is a part of the support frame, wherein the support frame comprises a support frame upper portion positioned in a correctly worn glasses above the eyes and extending between frame legs of the glasses, and wherein the support frame upper portion of the glasses is provided with the at least one light source.

12. The glasses of claim 1, wherein the frame above the spectacle glass is provided with at least one light guiding element for indirect delivery of light originating from the at least one light source substantially from above the spectacle glass to the eyes, wherein the frame of the glasses is provided with a support frame for supporting the spectacle glasses, wherein the nose frame part is a part of the support frame, wherein the support frame comprises a support frame upper portion positioned in a correctly worn glasses above the eyes and extending between frame legs of the glasses, wherein the support frame upper portion of the glasses is provided with the at least one light source, and wherein the support frame upper portion is provided with the light guiding element.

13. The glasses of claim 1, wherein the frame of the glasses is provided with a support frame for supporting the spectacle glasses, wherein the support frame comprises a support frame upper portion positioned in a correctly worn glasses above the eyes and extending between frame legs of the glasses, wherein the support frame of the frame encloses at least half the perimeter of the spectacle glasses, and wherein with a worn glasses the portion of the support frame positioned lower than the support frame upper portion at, at least, a side of the support frame that is facing the eye, at least partly reflects to the eye the incident light thereon directly or indirectly originating from the light source.

14. The glasses of claim 1, wherein the surface of at least the eye-facing nose frame side portion is at least partially configured to reflect the light to be reflected diffusely to the eye.

15. The glasses of claim 1, wherein at least a part of the eye-facing nose frame side portion is curved to direct to the eye the light to be reflected.

16. The glasses of claim 1, wherein at least the eye-facing nose frame side portion is at least partly provided with whitening agents.

17. The glasses of claim 1, wherein the frame is provided with a communication device such as, for example, a USB port for a wired connection and/or, for example, a Bluetooth chip for a wireless connection.

18. The glasses of claim 1, wherein the frame is provided with an actuator such as a circuit board (PCB), as well as a battery and optionally a memory storage.

19. A system comprising a glasses of claim 1, wherein the frame is provided with a communication device such as, for example, a USB port for a wired connection and/or, for example, a Bluetooth chip for a wireless connection, wherein the system further comprises an external device provided with a processor as well as a computer program which, in use, causes the processor to control the at least one light source in the glasses in accordance with a predetermined program, and wherein preferably the desired program is chosen by a wearer of the glasses.

* * * * *